(12) United States Patent
Kim

(10) Patent No.: US 7,716,771 B2
(45) Date of Patent: May 18, 2010

(54) COMMON TOOTHBRUSH USABLE ELECTRONIC TOOTHBRUSH

(76) Inventor: Nam Soo Kim, Gukjae Sanjang Apt., 104-204, Sinrim-Dong, Gwanak-Gu, Seoul (KR) 151-010

( * ) Notice: Subject to any disclaimer, the term of this patent is extended or adjusted under 35 U.S.C. 154(b) by 883 days.

(21) Appl. No.: 11/248,763

(22) Filed: Oct. 12, 2005

(65) Prior Publication Data
US 2006/0090274 A1 May 4, 2006

(30) Foreign Application Priority Data
Oct. 28, 2004 (KR) ............... 10-2004-0086426

(51) Int. Cl.
*A61C 17/22* (2006.01)
(52) U.S. Cl. ............................................ 15/21.1
(58) Field of Classification Search ............ 15/22.1, 15/22.2
See application file for complete search history.

(56) References Cited

U.S. PATENT DOCUMENTS

| | | | | |
|---|---|---|---|---|
| 2,875,458 A | * | 3/1959 | Tsuda ................... | 15/22.1 |
| 3,196,299 A | * | 7/1965 | Kott .................... | 310/81 |
| 3,316,576 A | * | 5/1967 | Urbush ................. | 15/22.1 |
| 5,283,921 A | * | 2/1994 | Ng ...................... | 15/22.1 |
| 5,689,850 A | * | 11/1997 | Shekalim ............... | 15/22.1 |

* cited by examiner

*Primary Examiner*—Laura C Guidotti
(74) *Attorney, Agent, or Firm*—Tutunjian & Bitetto, P.C.

(57) ABSTRACT

A common toothbrush usable electronic toothbrush is provided. The common toothbrush usable electronic toothbrush includes: a toothbrush receiving part having a housing for receiving a toothbrush and a fixing member for fixing the toothbrush; and a driving part tightly attached to the toothbrush receiving part, for vibrating the whole toothbrush by transmitting a vibration generated from a driving of a motor to the toothbrush receiving part. Since the electronic toothbrush can receive common toothbrushes of various kinds instead of a dedicated electric toothbrush, it is possible to permanently use the electronic toothbrush by replacing common toothbrushes, thus increasing a user's satisfaction by allowing a usage of toothbrushes as the user wishes.

9 Claims, 5 Drawing Sheets

COMMON TOOTHBRUSH USABLE ELECTRONIC TOOTHBRUSH

BACKGROUND OF THE INVENTION

1. Field of the Invention

The present invention relates to an electronic toothbrush, and more particularly, to a common toothbrush usable electronic toothbrush.

2. Description of the Related Art

In general, many electronic toothbrushes on the market have a set of a holder part and a toothbrush part. The holder part includes a driving unit to generate vibration. The toothbrush part is combined with the holder part. These conventional toothbrushes have to use a dedicated toothbrush that can be fitted into the holder part. Thus, when a disposable toothbrush is worn out and needs to be replaced, it is difficult to purchase the dedicated toothbrush only and is mandatory to buy a new set. As a result, purchasing a toothbrush becomes expensive.

Additionally, since only the dedicated toothbrush manufactured and sold as a set can be used, it is very hard to find an appropriate toothbrush for a replacement after awhile from the purchase of the toothbrush.

In an operation method of the conventional electronic toothbrush, a bristle of a toothbrush rotates in a circle or a head of a toothbrush rotates in a left and right direction. However, since a user's teeth can be brushed only according to an operation of the electronic toothbrush and the user cannot actively control the toothbrush, the user may not feel satisfied that a complete brushing has been performed after brushing his teeth. Additionally, since a neck of a dedicated toothbrush made for an electronic toothbrush is very thin, it is very hard to strongly grab the toothbrush for brushing teeth.

SUMMARY OF THE INVENTION

Accordingly, the present invention is directed to a common toothbrush usable electronic toothbrush that substantially obviates one or more problems due to limitations and disadvantages of the related art.

An object of the present invention is to provide an electronic toothbrush that is capable of mounting a common toothbrush of inexpensive purchase and maintenance cost by providing a toothbrush receiving part instead of a disposable toothbrush, receiving the common toothbrush in the toothbrush receiving part, and replacing the common toothbrush easily when it is worn out.

Another object of the present invention is to provide an electronic toothbrush that is capable of mounting a common toothbrush without being affected by a change of time and place after purchasing a toothbrush, and using the electronic toothbrush permanently by providing a common toothbrush instead of a dedicated toothbrush only made as a set.

A further object of the present invention is to provide the electronic toothbrush that is capable of mounting a common toothbrush providing more freshness or effective brushing by strongly grabbing the toothbrush for brushing teeth with the common toothbrush in the electronic toothbrush in order to make up for the drawback of difficulty of strongly grabbing the toothbrush because of weakness of a joint part and a neck of the toothbrush when using a conventional electronic toothbrush.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

To achieve these objects and other advantages and in accordance with the purpose of the invention, as embodied and broadly described herein, there is provided a common toothbrush usable electronic toothbrush, including: a toothbrush receiving part having a housing for receiving a toothbrush and a fixing member for fixing the toothbrush; and a driving part tightly attached to the toothbrush receiving part, for vibrating the whole toothbrush by transmitting a vibration generated from a driving of a motor to the toothbrush receiving part.

The toothbrush receiving part may include: a housing in which the toothbrush is received; a fixing member having a lower portion and an upper portion, the lower portion being fitted and attached into the housing, the upper portion having a plurality of split segments and a threaded portion, such that the split segments get closer when a fixing cap is put on and tightly fixes the toothbrush; a fixing cap for fixing the toothbrush in the housing by adjusting and tightening a gap between the split segments in the upper portion of the fixing member according to thickness of the toothbrush when threading with the fixing member, a tightening opening of the lower portion having a diameter smaller than that of the upper portion; and a stopper disposed at an inside of the toothbrush receiving part, for supporting the toothbrush in contact with an end portion of the toothbrush.

The toothbrush receiving part may include another fixing cap screwed at a lower portion thereof, the other fixing cap having a diameter different from that of the tightening opening in the upper portion.

The driving part may include: a case having a battery-motor assembly and an eccentric weight installed therein; an assembly having a motor and a battery case made in one body, the assembly driving the motor by an operation of an on/off switch; and an eccentric weight eccentrically connected with a motor shaft, the eccentric weight rotating according to a driving of the motor.

The eccentric weight may be eccentrically connected with the motor shaft and rotates according to a driving of the motor, such that the driving part is vibrated in all directions.

The driving part may include: a case having a recharging jack; a motor; an on/off switch; a rechargeable battery recharged through the recharging jack and driving the motor when the on/off switch is on; and an eccentric weight eccentrically connected with a motor shaft, the eccentric weight being rotated according to a driving of the motor, such that the electronic toothbrush is rechargeable.

It is to be understood that both the foregoing general description and the following detailed description of the present invention are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention. In the drawings.

DETAILED DESCRIPTION OF THE INVENTION

Reference will now be made in detail to the preferred embodiments of the present invention, examples of which are illustrated in the accompanying drawings. Wherever possible, the same reference numbers will be used throughout the drawings to refer to the same or like parts.

Figure 1:
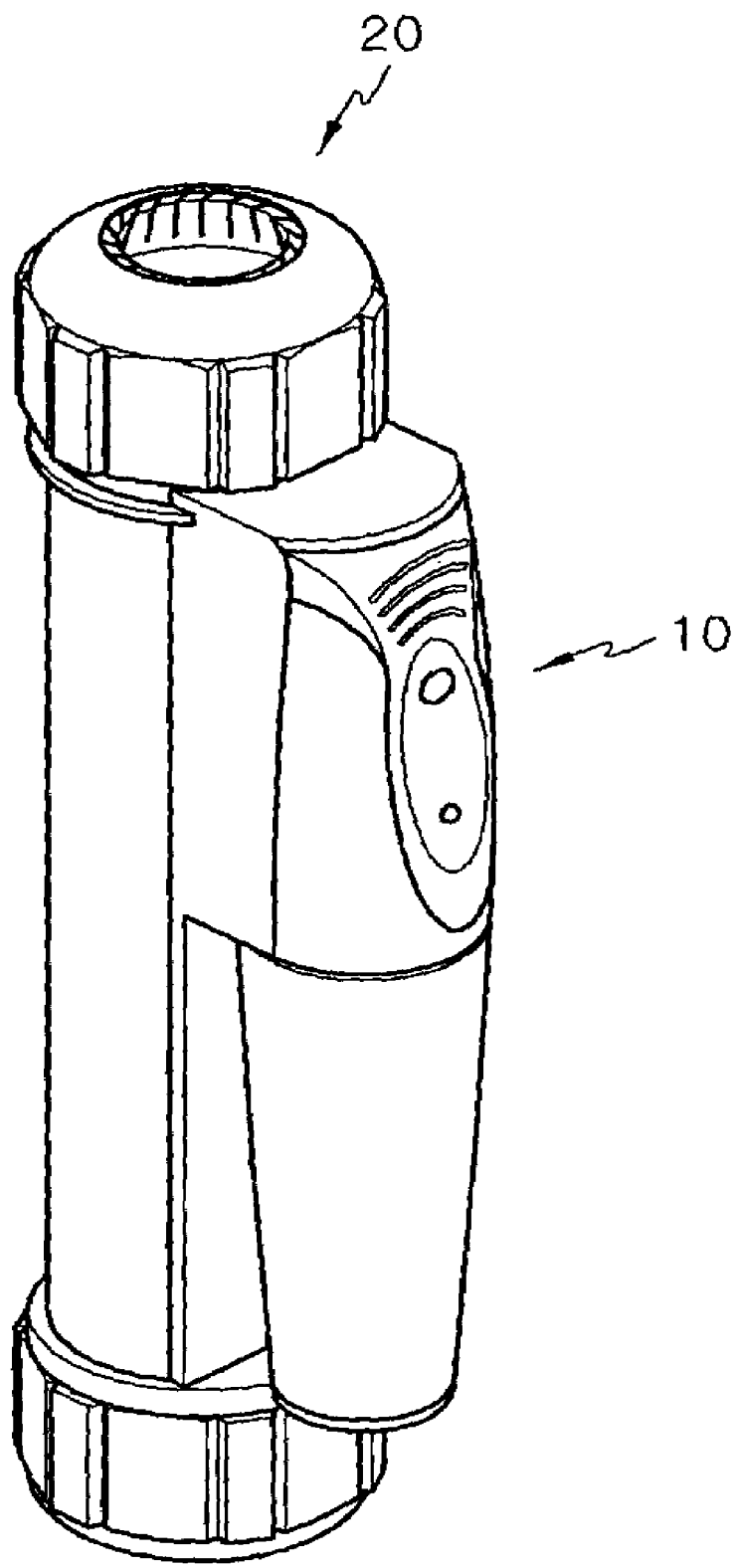
FIG. 1 is a perspective view of a common toothbrush usable electronic toothbrush according to an embodiment of the present invention.
Figure 2:
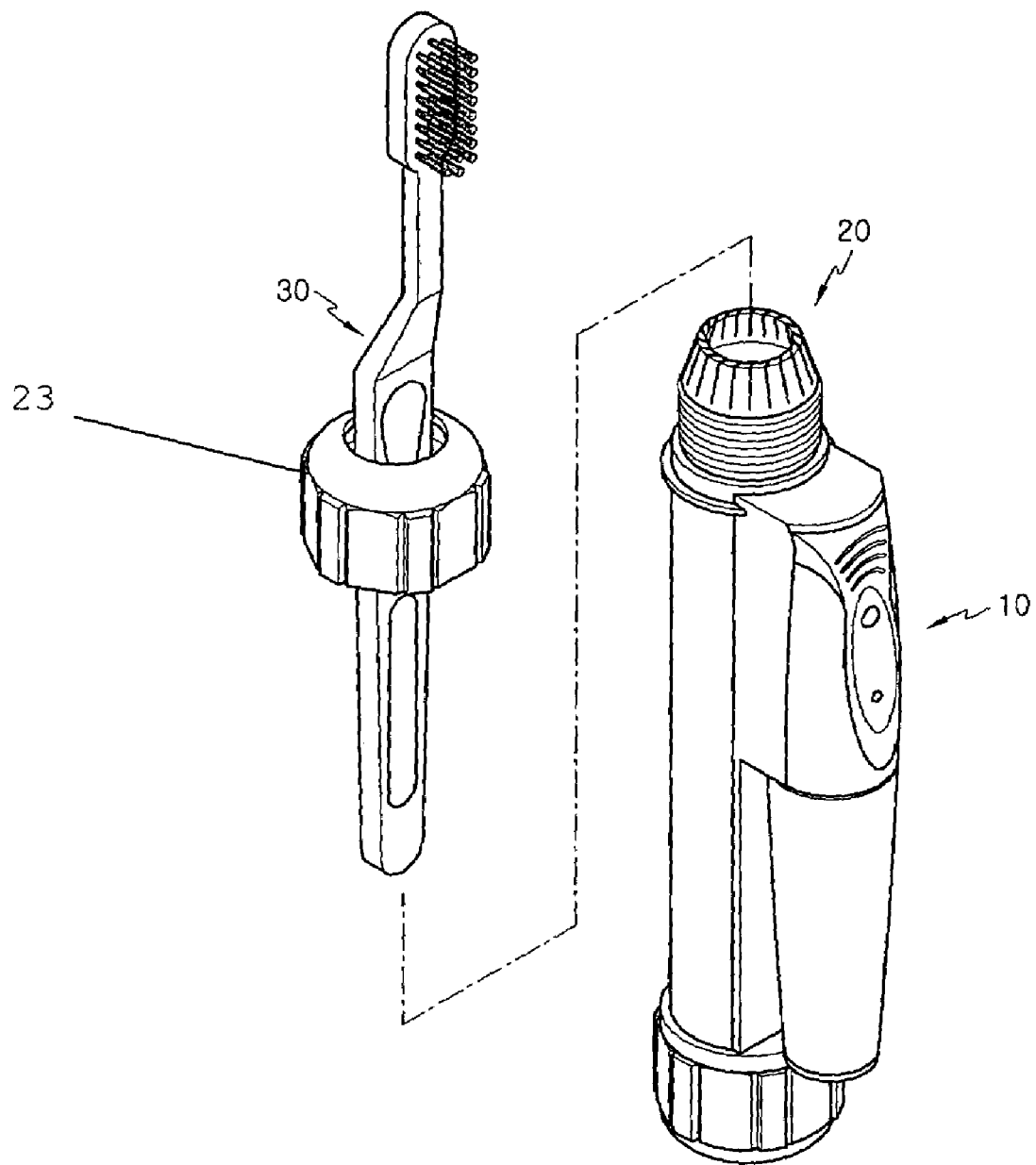
FIG. 2 is a usage view of when a common toothbrush is mounted in an electronic toothbrush according to an embodiment of the present invention.

FIGS. 1 and 2 are a perspective view and a usage view of a common toothbrush usable electronic toothbrush according to an embodiment of the present invention. Referring to FIGS. 1 and 2, the electronic toothbrush includes a driving part 10 and a toothbrush receiving part 20. A toothbrush 30 is held into the toothbrush receiving part 20 and is fixed by a fixing cap 23.

Figure 3:
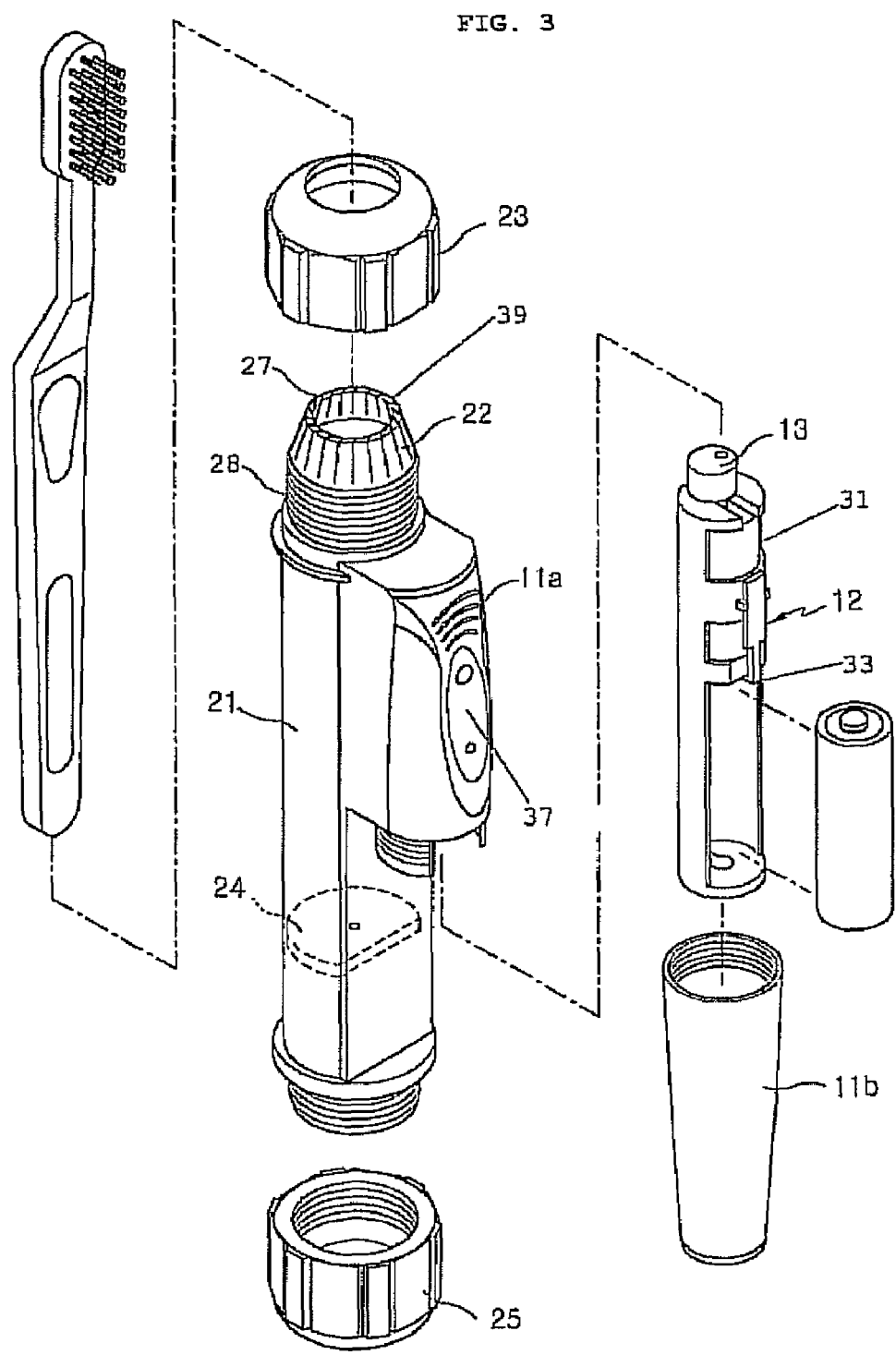
FIG. 3 is an exploded perspective view of a common toothbrush usable electronic toothbrush according to an embodiment of the present invention.

FIG. 3 is an exploded perspective view of a common toothbrush usable electronic toothbrush including the driving part 10 (FIG. 2) and the toothbrush receiving part 20.

Referring to FIG. 3, the driving part 10 includes cases 11a and 11b, an assembly 12 with a motor 31 and a battery case 33 provided in one body, and an eccentric weight 13. Additionally, the driving part 10 is tightly connected to the toothbrush receiving part 20. The cases 11a and 11b include the upper case 11a made in one body together with the toothbrush receiving part 20, and the lower case 11b detachably connected with the upper case 11a using a screw. Thus, once the lower case 11b is detached, the assembly 12 can be easily installed inside the upper case 11a.

An on/off switch 37 that operates the electronic toothbrush is installed in the upper case 11a. When the assembly 12 and a motor are internally installed in the upper case 11a, the on/off switch contacts with a driving on/off device installed in the assembly 12, such that it switches on/off the motor.

The assembly 12 has a driving motor 31 and a battery case 33. An eccentric weight is eccentrically connected to a rotational shaft of the motor. As shown in FIG. 3, the battery case and the motor can be made in one body, or the battery case can be separately manufactured. The battery case makes it easy to replace a disposable battery.

Figure 4:
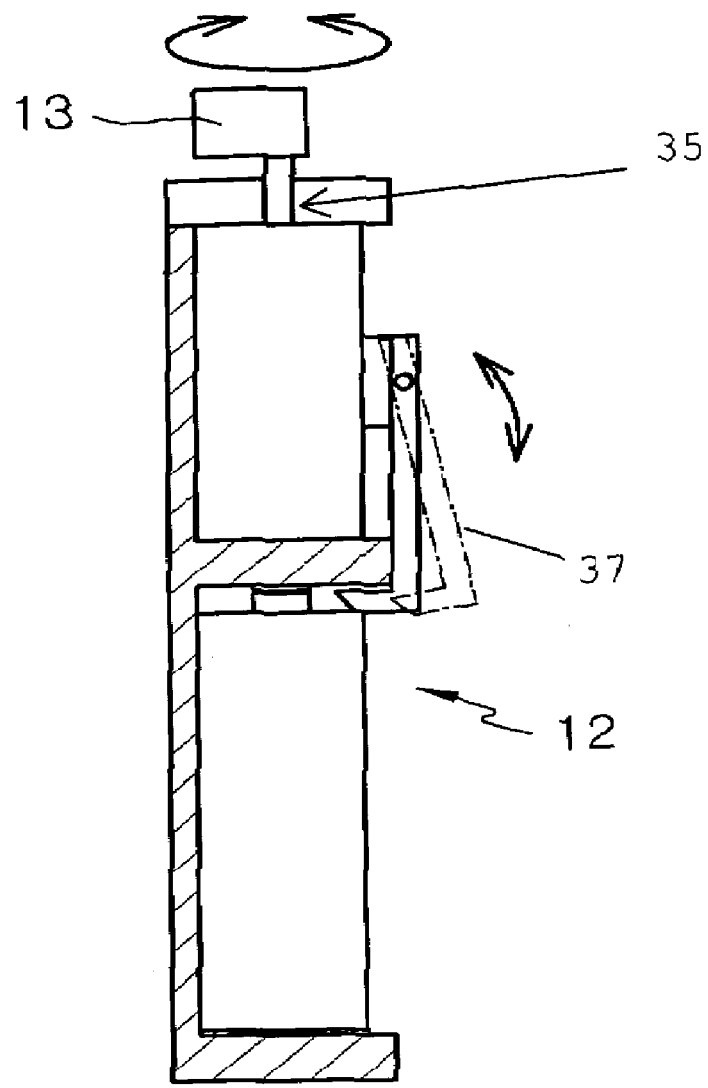
FIG. 4 is a sectional view of an eccentric weight and a battery-driven motor assembly.

Referring to FIG. 4, when an assembly on/off device installed on the side of the assembly 12 is switched on to rotate the motor, an eccentric weight 13 rotates on a shaft 35 according to a rotation of the motor 31. Accordingly, not only the assembly 12 but also the cases 11a and 11b and the whole body of an electronic toothbrush are vibrated in all directions.

Referring again to FIG. 3, the toothbrush receiving part 20 includes a housing 21, a fixing member 22, a fixing cap 23, and a stopper 24.

The housing 21 has a long inner space to receive a toothbrush and the fixing member 22 is installed in an upper portion of the housing 21.

A lower portion 28 of the fixing member 22 is fitted into and attached to an upper end portion of the housing 21. A middle part thereof has a threaded portion for a screw connection. Additionally, the upper portion 27 of the fixing member 22 uses materials such as a resilient rubber and has split segments 39 at the end portion thereof, such that a gap between the split segments can be adjusted. Since the upper portion 27 of the fixing member 22 is slanted toward the inside, various toothbrushes can be fitted into the toothbrush receiving part 20.

Additionally, the fixing cap 23 fixes the toothbrush that is received in the fixing member 22 after the toothbrush is placed in the housing 21 through the fixing member 22. Since the inner diameter of the upper portion 27 is smaller than that of the lower portion 28 in the fixing member 22, the upper portion 27 of the fixing member 22 is fitted into the tightening opening of the upper portion in the fixing cap 23 to thereby fix the toothbrush. Accordingly, when the fixing cap 23 and fixing member 22 are combined with each other, it is possible to adjust a degree of a combination by using a screw according to a thickness of the toothbrush. As a result, the toothbrush is tightly fixed so that various kinds of toothbrushes can be used.

The stopper 24 is installed in the inside of the toothbrush receiving part 20. The stopper 24 is in contact with the end portion of the toothbrush when the toothbrush is fixedly fitted in the toothbrush receiving part 20. Additionally, the stopper 24 adjusts a degree of insertion of the toothbrush and tightly fixes the toothbrush at the same time. For this purpose, the stopper 24 is needed to be closely attached to the inside of the receiving part 20, and a portion contacting with the end portion of the toothbrush needs to be concavely slanted toward a center of the stopper 24 to support and fix the toothbrush. Additionally, it is preferable that a center portion of the stopper 24 has an opening to easily wash the inside of the housing 21.

It is possible to make a threaded portion having an identical diameter of the fixing member 22 to attach another fixing cap 25 at the lower portion of the housing 21. Consequently, another fixing cap 25 can be attached to the bottom of the toothbrush receiving part 20. Another fixing cap 25 has an identical diameter of the lower portion in the fixing cap 23 but a different diameter of the tightening opening in the fixing cap 23. Accordingly, when there is a large difference between thicknesses of the various toothbrushes, one of the two fixing caps can be chosen to tightly fix the toothbrush.

Figure 5:
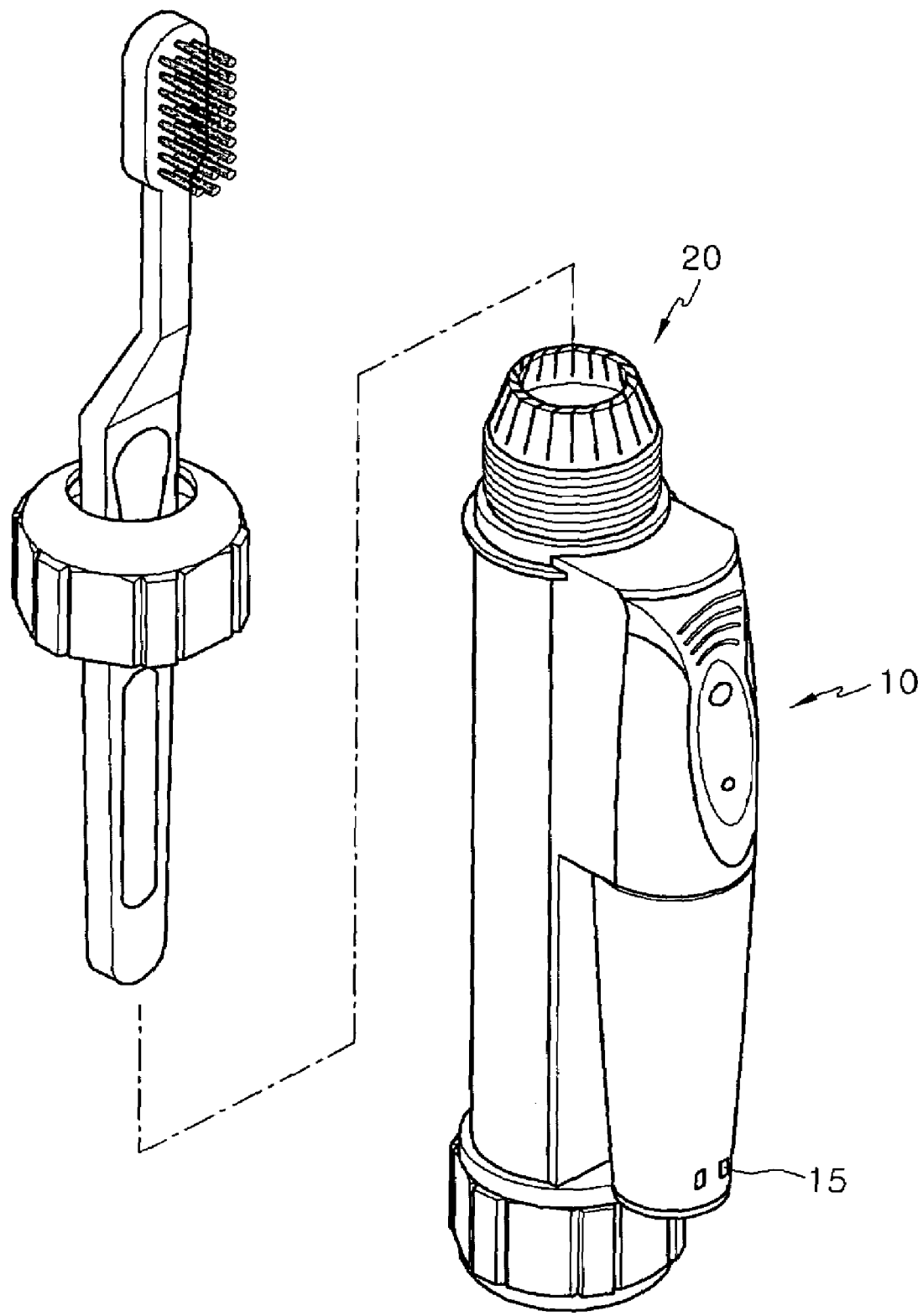
FIG. 5 is a usage view of a common toothbrush usable electronic toothbrush according to another embodiment of the present invention.

FIG. 5 is a perspective view of a common toothbrush usable electronic toothbrush according to another embodiment of the present invention.

Referring to FIG. 5, the electronic toothbrush uses a rechargeable battery and a motor, instead of the battery-motor assembly 12 included in the driving part 10. The electronic toothbrush includes a recharging jack 15 disposed at an exterior of the case 11b, such that it can be used semi-permanently by the recharging. In this embodiment, since all the components except the driving part are identical to the above-described embodiment, a description thereof will be omitted.

According to the inventive common toothbrush usable electronic toothbrush, various common toothbrushes can be used instead of a dedicated toothbrush that is made and sold as a set. Also, the electronic toothbrush is not affected by a change of time and place after purchasing a toothbrush and can be permanently used by replacing the toothbrush. Further, the cost of purchase and maintenance in use can be reduced.

A user can brush teeth in a desired manner by using the operation of the electronic toothbrush. Also the user can brush effectively each corner and facet of tooth by shaking of the whole body in all directions according to vibration of the eccentric weight. Consequently, the electronic toothbrush according to the invention provides more freshness and effectiveness, compared with a conventional electronic toothbrush.

It will be apparent to those skilled in the art that various modifications and variations can be made in the present invention. Thus, it is intended that the present invention covers the modifications and variations of this invention provided they come within the scope of the appended claims and their equivalents.

What is claimed is:

1. A device for converting a conventional toothbrush to an electronic toothbrush comprising:
   a toothbrush receiving part having a housing for receiving a common toothbrush with a stopper for supporting the common toothbrush disposed at an inside of the toothbrush receiving part such that the stopper is in direct contact with an end portion of the common toothbrush;
   a fixing member for fixing the toothbrush wherein the fixing member having a lower portion and an upper portion, the lower portion being fitted and attached into the housing, the upper portion having a plurality of radially arranged split segments and a threaded portion, such that the split segments get closer when a fixing cap is put on and tightly fixes the toothbrush; and
   a driving part tightly attached to the toothbrush receiving part, for vibrating the whole toothbrush by transmitting a vibration generated from a driving of a motor to the toothbrush receiving part.

2. The device for converting a conventional toothbrush to an electronic toothbrush of claim 1, wherein the toothbrush receiving part further comprises:
   a fixing cap For fixing the toothbrush in the housing by adjusting and tightening a gap between the split segments in the upper portion of the fixing member according to thickness of the toothbrush when threaded with the fixing member, a tightening opening of the lower portion having a diameter larger than that of the upper portion; and
   an opening in the stopper disposed at an inside of the toothbrush receiving part, for washing the inside of the housing.

3. The device for converting a conventional toothbrush to an electronic toothbrush of claim 2, wherein the toothbrush receiving part includes a second fixing cap threaded at a lower portion thereof, the second fixing cap having a diameter different from that of the tightening opening in the upper portion.

4. The device for converting a conventional toothbrush to an electronic toothbrush of claim 1, wherein the driving part further comprises:
   an assembly having a motor with a shaft and a battery within a case made in one body, said assembly driving the motor by an operation of an on/off switch; and
   an eccentric weight eccentrically connected with the motor shaft, the eccentric weight rotating according to diving of the motor to generate vibration.

5. The device for converting a conventional toothbrush to an electronic toothbrush of claim 1, wherein the driving part further comprises:
   a case having a recharging jack;
   a motor with a shaft; an on/off switch;
   a rechargeable battery recharged through the recharging jack and driving the motor when the on/off switch is on; and
   an eccentric weight eccentrically connected with the motor shaft, the eccentric weight rotating according to diving of the motor to generate vibration.

6. A common toothbrush using electronic toothbrush, comprising:
   a toothbrush receiving part having a housing for receiving a common toothbrush with a stopper for supporting the common toothbrush disposed at an inside of the toothbrush receiving part such that the stopper is in direct contact with an end portion of the common toothbrush, wherein the stopper adjusts a degree of insertion of the common toothbrush, wherein the toothbrush receiving part comprises: the housing in which the toothbrush is received; the fixing member having a lower portion and an upper portion, the lower portion being fitted and attached into the housing, the upper portion having a plurality of split segments and a threaded portion, such that the split segments get closer when a fixing cap is put on and tightly fixes the toothbrush; a fixing cap For fixing the toothbrush in the housing by adjusting and tightening a gap between the split segments in the upper portion of the fixing member according to thickness of the toothbrush when threaded with the fixing member, a tightening opening of the lower portion having a diameter larger than that of the upper portion, wherein the toothbrush receiving part includes a second fixing cap threaded at a lower portion thereof, the second fixing cap having a diameter different from that of the tightening opening in the upper portion;
   a fixing member for fixing the toothbrush; and
   a driving part tightly attached to the toothbrush receiving part, for vibrating the whole toothbrush by transmitting a vibration generated from a driving of a motor to the toothbrush receiving part.

7. The common toothbrush using electronic toothbrush of claim 6, wherein the driving part comprises:
   an assembly having a motor and a battery within a case made in one body, said assembly driving the motor by an operation of an on/off switch; and
   an eccentric weight eccentrically connected with a motor shaft, the eccentric weight rotating according to a driving of the motor.

8. The common toothbrush using electrical toothbrush of claim 7, wherein the eccentric weight is eccentrically connected with the motor shaft and rotates according to a diving of the motor, such that the driving part is vibrated in all directions.

9. The common toothbrush using electrical toothbrush of claim 6, wherein the driving part comprises: a case having a recharging jack; a motor; an on/off switch; a rechargeable battery recharged through the recharging jack and driving the motor when the on/off switch is on; and an eccentric weight eccentrically connected with a motor shaft, the eccentric weight being rotated according to a driving of the motor, such that the electronic toothbrush is rechargeable.

* * * * *